US006309668B1

(12) United States Patent
Bastin et al.

(10) Patent No.: US 6,309,668 B1
(45) Date of Patent: Oct. 30, 2001

(54) ABUSE RESISTANT TABLETS

(75) Inventors: Richard James Bastin; Bruce Hamilton Lithgow, both of Dagenham (GB)

(73) Assignee: Aventis Pharma Limited, West Malling (GB)

( * ) Notice: Subject to any disclaimer, the term of this patent is extended or adjusted under 35 U.S.C. 154(b) by 0 days.

(21) Appl. No.: 08/676,113

(22) PCT Filed: Jan. 24, 1995

(86) PCT No.: PCT/GB95/00137

§ 371 Date: Jul. 30, 1996

§ 102(e) Date: Jul. 30, 1996

(87) PCT Pub. No.: WO95/20947

PCT Pub. Date: Aug. 10, 1995

(30) Foreign Application Priority Data

Feb. 1, 1994 (GB) .................................................. 9401894

(51) Int. Cl.[7] ...................................................... A61K 9/34
(52) U.S. Cl. ........................... 424/472; 424/474; 424/479; 424/480; 424/481
(58) Field of Search ..................... 424/489, 456, 424/35, 464, 480, 482, 472, 440, 458

(56) References Cited

U.S. PATENT DOCUMENTS

| 3,980,766 | | 9/1976 | Shaw et al. . |
| 4,070,494 | | 1/1978 | Hoffmeister et al. . |
| 4,462,982 | * | 7/1984 | Samejima et al. ...................... 424/35 |
| 4,728,512 | * | 3/1988 | Mehta et al. .......................... 424/458 |
| 4,753,790 | * | 6/1988 | Silva et al. ............................ 424/440 |
| 4,814,178 | * | 3/1989 | Bolton et al. ......................... 424/467 |
| 4,828,840 | | 5/1989 | Sakamoto et al. . |
| 4,865,849 | | 9/1989 | Ubaldo et al. . |
| 4,966,772 | | 10/1990 | Ohm et al. . |
| 5,417,985 | * | 5/1995 | Coutel et al. ......................... 424/489 |
| 5,474,784 | * | 12/1995 | Stevens et al. ....................... 424/456 |

FOREIGN PATENT DOCUMENTS

| 664908 | 8/1938 | (DE) . |
| 0 546 593 | 6/1993 | (EP) . |
| 2203338 | 10/1988 | (GB) . |
| 63-44125 | 9/1988 | (JP) . |
| WO 94/06416 | 3/1994 | (WO) . |

* cited by examiner

Primary Examiner—Thurman K. Page
Assistant Examiner—R. Joynes
(74) Attorney, Agent, or Firm—Ross J. Oehler; George G. Wang

(57) ABSTRACT

This invention relates to an abuse resistant tablet containing two or more layers having one or more drugs and one or more gelling agents and its preparation. The drug(s) and gelling agent(s) are in separate layers of the tablet. The multilayer tablet is particularly suitable for the administration of drugs prone to abuse by unauthorized parenteral administration such as analgesics, hypnotics, and anxiolytics.

22 Claims, No Drawings

ABUSE RESISTANT TABLETS

This application is a 371 of PCT/GB95/00137 filed Jan. 24, 1995.

This invention relates to abuse resistant tablets, to a process for their preparation, and to their use in therapy. More particularly, the present invention relates to abuse resistant tablets comprising a plurality of layers.

It is known that many drugs intended for legitimate oral use have the potential for abuse, whereby the drug may be extracted from a solid oral dosage form to provide a solution which may be used for unauthorised, unsupervised, illegal and/or dangerous parenteral administration. One way of substantially reducing or even eliminating this potential for drug abuse is to suppress or inhibit the extractibility of the drug from the composition comprising the drug. In U.S. Pat. No. 4,070,494 this is reported to have been achieved by incorporating in the composition an aqueous gelable material present in sufficient quantity to form a gel when combined with that volume of water otherwise necessary to dissolve all of the medicinal agent. U.S. Pat. No. 4,070,494 describes enteral compositions, including single and bilayer tablets, wherein the drug with potential for abuse is mixed with the gelling agent and in the case of a tablet is then pressed according to a conventional procedure. However, such tablets comprising a gelling layer are liable to seriously retard the release of the drug substance.

We have now found that release of the drug substance from a tablet comprising a gelling agent is improved if the drug substance and the gelling agent are present in separate layers of the tablet.

The present invention thus pertains to a tablet containing two or more layers comprising one or more drugs and one or more gelling agents, characterised in that the drug(s) and gelling agent(s) are contained in separate layers of the tablet.

For the avoidance of doubt, it should be appreciated that the tablet may comprise separate layers one stacked on top of the other in a sandwich arrangement, or may comprise a core layer of gelling agent surrounded by one or more layers comprising one or more drugs. The sandwich arrangement is generally preferred.

Optionally the tablet has a coating which may or may not be a modified or sustained release coating.

Suitable drugs which may be incorporated into the abuse resistant tablets of the present invention include those which are particularly liable to abuse, for example, analgesics, hypnotics and anxiolytics.

Specific examples of analgesic drugs which may be incorporated into tablets of this invention include commercially available analgesic drugs, such as codeine, pethidine, methadone and morphine.

Specific examples of hypnotic agents which may be incorporated into tablets of this invention include benzodiazepines such as temazepam, nitrazepam, flurazepam and loprazolam and non-benzodiazepines such as chlormethiazole, zopiclone and zolpidem, and barbiturates such as butobarbitone, phenobarbitone and amylobarbitone.

Specific examples of anxiolytic agents which may be incorporated into tablets of this invention include diazepam, medazepam, oxazepam and lorazepam.

The term "gelling agent" as used herein refers to a material which forms a gel by the action of an aqueous medium, such as water or an aqueous solution of an organic acid (e.g. aqueous citric or acetic acid), a base (e.g. sodium bicarbonate or sodium tetraborate solution) or alcohol (e.g. an aqueous lower alkanol such as aqueous ethanol or isopropanol).

Suitable gelling agents include, but are not limited to, modified celluloses such as hydroxypropylmethylcellulose, hydroxypropyl-ethylcellulose, methylcellulose, sodium carboxymethylcellulose, and hydroxyethylcellulose, sodium alginate, alginic acid, tragacanth, polyacrylic acid and xanthan, guar, locust bean and karaya gums. Mixtures of two or more gelling agents may also be used.

Hereinafter, the layer or layers of the tablet containing the drug is referred to as the "active layer" and the layer or layers containing the gelling agent is referred to as the "gelling layer".

The viscosity of the gelling agent in the gelling layer will generally be within the range of about 1000 cp to about 100,000 cp. As used herein, the term "cp" refers to centipoise which is a standard unit of viscosity. One centipoise (cp) is equivalent to one millipascal second (mPa.s).

Preferably, the gelling agent will have a viscosity within the range of about 4,000 cp to about 100,000 cp. More preferably, the gelling agent will have a viscosity within the range of about 10,000 cp to about 100,000 cp.

It will be appreciated that the amount of gelling agent required in the tablet depends upon features such as the nature of the active constituent, the nature of the other excipients in the tablet, the weight of the tablet and the viscosity grade of the gelling agent. The amount of gelling agent present is preferably such that substantially no filterable material remains when the tablet is triturated with the minimal amount of aqueous medium needed to extract the drug. In general, the proportion of gelling agent by weight in the gelling layer is from about 10 to about 70%, preferably about 20 to about 60%, and most preferably about 30 to about 50%. The total amount of gelling layer in the tablet depends upon the relative proportion of active and gelling layers but may typically be in the range of about 20 to about 80% and preferably about 50 to about 80% by weight.

The amount of drug in the active layer depends upon the therapeutic dose required, as in conventional tablets. In general, the quantity of drug which is incorporated into each tablet is often from about 0.5 mg to about 200 mg by weight, preferably from about 1 mg to about 100 mg, and most preferably from about 1 mg to about 50 mg. In the case of zopiclone the quantity of drug which is incorporated into each tablet is preferably about 1 mg to about 10 mg.

The remainder of the active and gelling layers may consist of standard tablet excipients known to those in the art, including but not limited to diluents such as lactose, starches, cellulose and calcium hydrogen phosphate, disintegrants such as starches, modified starches, celluloses and modified celluloses, binders, glidants and lubricants.

The tablet may also contain materials known in the art intended for the modification of release characteristics of the drug.

Preferably the active layer and the gelling layer are substantially identical in colour and appearance, so that the join is not readily visible to the potential abuser.

A coating, which may or may not be a modified or sustained release coating, may advantageously be applied to a tablet according to the present invention. A coated tablet is potentially advantageous when the tablet layers are stacked in a sandwich construction in that the join between the active layer and the gelling layer is further disguised.

In tablets according to the invention with more than two layers, one surface of the active layer should be exposed to prevent retardation of release of drug substance. Since one surface of the active layer is always exposed and not in contact with the gelling layer in tablets according to the present invention, release of drug can proceed relatively uninhibited and at a rate substantially similar to that of conventional tablets which do not possess a gelling layer.

In contrast, a combination of the active drug substance and gelling agent in the same layer has the disadvantage that the gelling action is likely to retard the release of the drug in a manner similar to some known sustained release products which include water-swellable high molecular weight polymers to retard drug release. Reduction of the gelling agent concentration to a level which would not inhibit release of the drug substance severely limits the abuse resistance potential of the tablet.

Drugs which may be particularly suitable for incorporation into the active layer of a tablet according to the present invention include zopiclone, temazepam, diazepam, zolpidem, codeine, methadone, pethidine, phenytoin and phenobarbitone. A preferred drug for use according to the present invention is zopiclone.

Gelling agents which may be particularly suitable for incorporation into the gelling layer of a tablet according to the present invention include modified celluloses and other high molecular weight polymers. Preferred gelling agents include modified celluloses such as hydroxypropylmethylcellulose, carboxymethylcellulose and methylcellulose and xanthan gum, especially hydroxypropylmethylcellulose.

A preferred tablet of the present invention is a bilayer tablet in which one layer comprises a drug and the other layer comprises a gelling agent. However, the invention also covers further multilayered tablets such as trilayered tablets.

It is to be understood that the present invention covers all appropriate combinations of particular and preferred moieties comprised within a tablet of the present invention as described herein.

According to a further feature of the invention there is provided a process for the preparation of a tablet of the present invention, which comprises forming the separate active and gelling layers, then combining the layers in a suitable tabletting machine, optionally followed by the application of a coating using a conventional coating procedure.

Tablets of the sandwich arrangement may conveniently be prepared by a multistage compression process using a suitable tablet press, where the first layer is compressed from a suitable powder and one or more additional layers are compressed on top of the first or subsequent layers to form a bilayer or multilayer tablet.

Tablets comprising a core of gelling layer surrounded by an active layer may conveniently be prepared by first forming the core from a suitable powder by compressing the powder using a suitable tablet press. Thereafter, the core may be enclosed within the active layer or surrounded by a cap of active layer using conventional means, such as using a tablet press designed for compression coating.

Presses for the preparation of multilayer tablets according to the present invention are either commercially available or may be provided by modification of standard tabletting equipment.

Suitable coatings for tablets of the present invention include film coatings to provide immediate release of the drug. Suitable film forming materials include hydroxypropylmethylcellulose, hydroxypropylcellulose, hydroxyethylcellulose, methylcellulose, polyvinylpyrrolidone, polyethylene glycols and acrylic polymers. Suitable film forming materials to provide modified or sustained release include ethylcellulose, fats and waxes, shellac, acrylic esters and phthalate or mellitate derivatives of cellulose ethers and polyvinyl ethers. The flexibility and performance of the film coat may be improved by the addition of plasticisers such as polyhydric alcohols, acetate and phthalate esters, glycerides and oils.

According to a further aspect of the present invention there is provided a method of treating a patient requiring an, analgesic, hypnotic or anxiolytic drug, which method comprises administering to said patient said drug comprised within a tablet according to the invention.

The following Examples illustrate the invention, but are not intended to limit the invention in any way.

EXAMPLE 1

| Part A | |
|---|---|
| Zopiclone | 6.00% w/w |
| Lactose | 18.52% w/w |
| Calcium hydrogen phosphate | 35.12% w/w |
| Maize starch | 35.12% w/w |
| Sodium starch glycollate | 5.00% w/w |
| Magnesium stearate | 0.24% w/w |

The components, with the exception of the magnesium stearate and the maize starch, were mixed together and then granulated using a paste containing the maize starch. The granules were dried, screened to obtain a suitable particle size distribution and mixed with the magnesium stearate.

| Part B | |
|---|---|
| Hydroxypropylmethylcellulose (100,000 cp) | 30.0% w/w |
| Calcium hydrogen phosphate | 59.2% w/w |
| Croscarmellose sodium | 10.0% w/w |
| Colloidal silica | 0.3% w/w |
| Magnesium stearate | 0.5% w/w |

The components, except the magnesium stearate, were mixed together in a blender. When these had been sufficiently blended the magnesium stearate was mixed with the powder.

Bilayer tablets each containing 7.5 mg of zopiclone, weighing 375 mg and containing 125 mg of Part A and 250 mg of Part B, and 9 mm in diameter, were produced on a tablet press by a two stage pressing procedure whereby tablets of Part B were formed in the press and then Part A was added and the press operated again.

EXAMPLE 2

| Part A | |
|---|---|
| Zopiclone | 6.0% w/w |
| Lactose | 30.8% w/w |
| Calcium hydrogen phosphate | 61.4% w/w |
| Sodium starch glycollate | 1.0% w/w |
| Colliodal silicon dioxide | 0.30% w/w |
| Magnesium stearate | 0.59% w/w |

The components, except the magnesium stearate, are mixed together in a blender. When these have been sufficiently blended the magnesium stearate is mixed with the powder.

| Part B | |
|---|---|
| Hydroxypropylmethylcellulose (100,000 cp) | 40.0% w/w |
| Calcium hydrogen phosphate | 49.2% w/w |
| Croscarmellose sodium | 10.0% w/w |
| Colloidal silicon dioxide | 0.3% w/w |
| Magnesium stearate | 0.5% w/w |

The components, with the exception of the magnesium stearate, are blended together. When these have been sufficiently blended the magnesium stearate is mixed with the powder. The powder is compressed by means of a tablet press and the tablets are subsequently sieved through a 1.5 mm screen to provide a coarse powder.

Bilayer tablets each containing 7.5 mg of zopiclone, weighing 375 mg and containing 125 mg of Part A and 250 mg of Part B, and 9 mm in diameter, are produced on a tablet press by a two stage pressing procedure whereby tablets of Part B are formed in the press and then Part A is added and the press is operated again.

EXAMPLE 3

| Part A | |
|---|---|
| Zopiclone | 6.0% w/w |
| Microcrystalline cellulose | 25.0% w/w |
| Lactose | 67.2% w/w |
| Sodium starch glycollate | 1.0% w/w |
| Colloidal silicon dioxide | 0.3% w/w |
| Magnesium stearate | 0.5% w/w |

The components, except the magnesium stearate, were mixed together in a blender. When these had been sufficiently blended the magnesium stearate was mixed with the powder.

| Part B | |
|---|---|
| Sodium carboxymethylcellulose (2,000 cp) | 35.0% w/w |
| Lactose | 54.2% w/w |
| Sodium starch glycollate | 10.0% w/w |
| Colloidal silicon dioxide | 0.3% w/w |
| Magnesium stearate | 0.5% w/w |

The components, except the magnesium stearate, were mixed together in a blender. When these had been sufficiently blended, the magnesium stearate was mixed with the powder.

Bilayer tablets each containing 7.5 mg of zopiclone, weighing 375 mg and containing 125 mg of Part A and 250 mg of Part B, and 9 mm in diameter, are produced on a tablet press by a two stage pressing procedure whereby tablets of Part B were formed in the press and then Part A was added and the press operated again.

EXAMPLE 4

| Part A | |
|---|---|
| Zopiclone | 6.00% w/w |
| Calcium hydrogen phosphate | 92.2% w/w |
| Croscarmellose sodium | 1.00% w/w |
| Colloidal silicon dioxide | 0.3% w/w |
| Magnesium stearate | 0.5% w/w |

The components, except the magnesium stearate, were mixed together in a blender. When these had been sufficiently blended the magnesium stearate was mixed with the powder.

| Part B | |
|---|---|
| Methylcellulose (4,000 cp) | 24.6% w/w |
| Lactose | 24.9% w/w |
| Calcium hydrogen phosphate | 40.0% w/w |
| Croscarmellose sodium | 10.0% w/w |
| Magnesium stearate | 0.5% w/w |

The components, except the magnesium stearate, were mixed together in a blender. When these had been sufficiently blended, the magnesium stearate was mixed with the powder.

Bilayer tablets each containing 7.5 mg of zopiclone, weighing 375 mg and containing 125 mg of Part A and 250 mg of Part B, and 9 mm in diameter, were produced on a tablet press by a two stage pressing procedure whereby tablets of Part B were formed in the press and then Part A was added and the press operated again.

EXAMPLE 5

| Part A | |
|---|---|
| Zopiclone | 6.0% w/w |
| Lactose | 30.3% w/w |
| Calcium hydrogen phosphate | 60.7% w/w |
| Sodium starch glycollate | 2.5% w/w |
| Magnesium stearate | 0.5% w/w |

The components, except the magnesium stearate, were mixed together in a blender. When these had been sufficiently blended the magnesium stearate was mixed with the powder.

| Part B | |
|---|---|
| Xanthan Gum | 30.0% w/w |
| Calcium hydrogen phosphate | 59.2% w/w |
| Croscarmellose sodium | 10.0% w/w |
| Colloidal silicon dioxide | 0.3% w/w |
| Magnesium stearate | 0.5% w/w |

The components, except the magnesium stearate, were mixed together in a blender. When these had been sufficiently blended the magnesium stearate was mixed with the powder.

Bilayer tablets each containing 7.5 mg of zopiclone, weighing 375 mg and containing 125 mg of Part A and 250 mg of Part B, and 9 mm in diameter, were produced on a tablet press by a two stage pressing procedure whereby tablets of Part B were formed in the press and then Part A was added and the press operated again.

EXAMPLE 6

| Part A | |
|---|---|
| Zopiclone | 6.0% w/w |
| Calcium hydrogen phosphate | 58.5% w/w |
| Microcrystalline cellulose | 30.0% w/w |
| Crospovidone | 5.0% w/w |
| Magnesium stearate | 0.5% w/w |

The components, with the exception of the magnesium stearate, are mixed together in a blender. When these have been sufficiently blended, the magnesium stearate is mixed with the powder.

| Part B | |
|---|---|
| Hydroxypropylmethylcellullose (100,000 cp) | 40.0% w/w |
| Calcium hydrogen phosphate | 19.2% w/w |
| Lactose | 29.0% w/w |
| Microcrystalline cellulose | 5.0% w/w |
| Povidone K30 | 6.0% w/w |
| Colloidal silicon dioxide | 0.3% w/w |
| Magnesium stearate | 0.5% w/w |

The components, with the exception of the colloidal silicon dioxide and the magnesium stearate, are blended together in a suitable mixer. The powder is then mixed with demineralised water until a granule is formed. The granule is dried and screened to obtain a satisfactory particle size. The screened granule is then blended with the colloidal silicon dioxide and the magnesium stearate.

Bilayer tablets, each containing 7.5 mg of zopiclone, weighing 325 mg and containing 125 mg of Part A and 200 mg of Part B and 9 mm in diameter, are produced on a tablet press by a two stage compression procedure.

Tablets are film coated by applying a coating solution containing hydroxypropylmethylcellulose, polyethylene glycol and colorants using a suitable coating apparatus.

EXAMPLE 7

| Part A | |
|---|---|
| Zopiclone | 4.5% w/w |
| Lactose | 19.4% w/w |
| Calcium Hydrogen Phosphate | 36.4% w/w |
| Maize starch | 36.4% w/w |
| Sodium starch glycollate | 3.0% w/w |
| Magnesium stearate | 0.3% w/w |

The zopiclone, lactose, calcium hydrogen phosphate and some of the maize starch were mixed together in a blender and then mixed with a paste prepared from the remaining starch and demineralised water until a granule was formed. The granule was dried and passed through a screen to obtain a satisfactory particle size. The screened granule was then blended with the sodium starch glycollate and the magnesium stearate.

| Part B | |
|---|---|
| Hydroxypropylmethylcellullose (100,000 cp) | 40.0% w/w |
| Calcium hydrogen phosphate | 19.2% w/w |
| Lactose | 29.0% w/w |
| Microcrystalline cellulose | 5.0% w/w |
| Povidone K30 | 6.0% w/w |
| Colloidal silicon dioxide | 0.3% w/w |
| Magnesium stearate | 0.5% w/w |

The components, with the exception of the colloidal silicon dioxide and the magnesium stearate, were blended together in a suitable mixer. The powder was then mixed with demineralised water until a granule was formed. The granule was dried and screened to obtain a satisfactory particle size. The screened granule was then blended with the colloidal silicon dioxide and the magnesium stearate.

(a) Bilayer tablets, each containing 7.5 mg of zopiclone, weighing 365 mg and containing 165 mg of Part A and 200 mg of Part B and 10 mm in diameter, were produced on a tablet press by a two stage compression procedure; and (b) Bilayer tablets, each containing 3.75 mg of zopiclone, weighing 283 mg and containing 83 mg of Part A and 200 mg of Part B and 9 mm in diameter, were produced on a tablet press by a two stage compression procedure.

Tablets from (a) and (b) above were film coated by applying a coating solution containing hydroxypropylmethylcellulose, polyethylene glycol and suitable colorants using a suitable coating apparatus.

EXAMPLE 8

| Part A | |
|---|---|
| Temazepam | 10.0% w/w |
| Anhydrous Lactose | 58.0% w/w |
| Microcryatalline cellulose | 25.0% w/w |
| Croscarmellose sodium | 6.0% w/w |
| Magnesium stearate | 1.0% w/w |

The components, with the exception of the magnesium stearate, are mixed together in a blender. When these have been sufficiently blended, the magnesium stearate is mixed with the powder.

| Part B | |
|---|---|
| Hydroxypropylmethylcellullose (100,000 cp) | 40.0% w/w |
| Lactose | 34.2% w/w |
| Microcrystalline cellulose | 25.0% w/w |
| Colloidal silicon dioxide | 0.3% w/w |
| Magnesium stearate | 0.5% w/w |

The components, with the exception of the colloidal silicon dioxide and the magnesium stearate, are blended together in a suitable mixer. The powder is then blended with the colloidal silicon dioxide and the magnesium stearate.

Bilayer tablets containing 20 mg of temazepam, weighing 400 mg and containing 200 mg of Part A and 200 mg of Part B, and 9 mm in diameter are produced on a tablet press by a two stage compression procedure.

EXAMPLE 9

| Part A | |
|---|---|
| Diazepam | 4.0% w/w |
| Lactose | 30.5% w/w |
| Calcium hydrogen phosphate | 35.0% w/w |
| Maize starch | 25.0% w/w |
| Croscarmellose sodium | 5.0% w/w |
| Magnesium stearate | 0.5% w/w |

The diazepam, lactose, calcium hydrogen phosphate and some of the maize starch and croscarmellose sodium are placed in a blender and then mixed with a paste prepared from the remaining starch and demineralised water until a granule is formed. The granule is dried and passed through a screen to obtain a satisfactory particle size. The screened granule is then blended with the remaining croscarmellose sodium and the magnesium stearate.

| Part B | |
|---|---|
| Hydroxypropylmethylcellullose (100,000 cp) | 40.0% w/w |
| Calcium hydrogen phospbate | 19.2% w/w |
| Lactose | 29.0% w/w |
| Microcrystalline cellulose | 5.0% w/w |
| Povidone K30 | 6.0% w/w |
| Colloidal silicon dioxide | 0.3% w/w |
| Magnesium stearate | 0.5% w/w |

The components, with the exception of the colloidal silicon dioxide and the magnesium stearate, are blended together in a suitable mixer. The powder is then mixed with demineralised water until a granule is formed. The granule is dried and screened to obtain a satisfactory particle size. The screened granule is then blended with the colloidal silicon dioxide and the magnesium stearate.

Bilayer tablets containing 5 mg of diazepam, weighing 325 mg and containing 125 mg of Part A and 200 mg of Part B, and 9 mm in diameter are produced on a tablet press by a two stage compression procedure.

EXAMPLE 10

| Part A | |
|---|---|
| Zolpidem hemitartrate | 5.0% w/w |
| Lactose | 64.5% w/w |
| Microcrystalline cellulose | 25.0% w/w |
| Croscarmellose sodium | 5.0% w/w |
| Magnesium stearate | 0.5% w/w |

The zolpidem hemitartrate, lactose and microcrystalline cellulose and croscarmellose sodium are mixed together in a blender. When these have been sufficiently blended, the magnesium stearate is mixed with the powder.

| Part B | |
|---|---|
| Hydroxypropylmethylcellullose (100,000 cp) | 40.0% w/w |
| Calcium hydrogen phosphate | 19.2% w/w |
| Lactose | 29.0% w/w |
| Microcrystalline cellulose | 5.0% w/w |
| Povidone K30 | 6.0% w/w |
| Colloidal silicon dioxide | 0.3% w/w |
| Magnesium stearate | 0.5% w/w |

The components, with the exception of the colloidal silicon dioxide and the magnesium stearate, are blended together in a suitable mixer. The powder is then mixed with demineralised water until a granule is formed. The granule is dried and screened to obtain a satisfactory particle size. The screened granule is then blended with the colloidal silicon dioxide and the magnesium stearate.

Bilayer tablets containing 5 mg of zolpidem hemitartrate, weighing 325 mg and containing 125 mg of Part A and 200 mg of Part B, and 9 mm in diameter are produced on a tablet press by a two stage compression procedure.

Tablets are film coated by applying a coating solution containing hydroxypropylmethylcellulose, polyethylene glycol and suitable colorants using a suitable coating apparatus.

EXAMPLE 11

| Part A | |
|---|---|
| Codeine Phosphate | 10.0% w/w |
| Lactose | 51.5% w/w |
| Maize starch | 30.0% w/w |
| Povidone K30 | 5.0% w/w |
| Sodium starch glycollate | 3.0% w/w |
| Magnesium stearate | 0.5% w/w |

The codeine phosphate, lactose, povidone and some of the maize starch are mixed together in a blender and then mixed with a paste prepared from the remaining starch and demineralised water until a granule is formed. The granule is dried and passed through a screen to obtain a satisfactory particle size. The screened granule is then blended with the sodium starch glycollate and the magnesium stearate.

| Part B | |
|---|---|
| Hydroxypropylmethylcellullose (100,000 cp) | 40.0% w/w |
| Calcium hydrogen phosphate | 19.2% w/w |
| Lactose | 29.0% w/w |
| Microcrystalline cellulose | 5.0% w/w |
| Povidone K30 | 6.0% w/w |
| Colloidal silicon dioxide | 0.3% w/w |
| Magnesium stearate | 0.5% w/w |

The components, with the exception of the colloidal silicon dioxide and the magnesium stearate, are blended together in a suitable mixer. The powder is then mixed with demineralised water until a granule is formed. The granule is dried and screened to obtain a satisfactory particle size. The screened granule is then blended with the colloidal silicon dioxide and the magnesium stearate.

Bilayer tablets containing 15 mg of codeine phosphate, weighing 350 mg and containing 150 mg of Part A and 200 mg of Part B, and 10 mm in diameter are produced on a tablet press by a two stage compression procedure.

EXAMPLE 12

| Part A | |
|---|---|
| Methadone hydrochloride | 5.0% w/w |
| Lactose | 39.0% w/w |
| Maize starch | 27.5% w/w |
| Powdered cellulose | 25.0% w/w |
| Sodium starch glycollate | 3.0% w/w |
| Magnesium stearate | 0.5% w/w |

The components, with the exception of the sodium starch glycollate and the magnesium stearate and some of the maize starch, are blended together in a suitable mixer. The powder is then mixed with a paste prepared from the remaining starch and demineralised water until a granule is formed. The granule is dried and screened to obtain a satisfactory particle size. The screened granule is then blended with the sodium starch glycollate and the magnesium stearate.

| Part B | |
|---|---|
| Hydroxypropylmethylcellullose (1000,000 cp) | 40.0% w/w |
| Calcium hydrogen phosphate | 19.2% w/w |
| Lactose | 29.0% w/w |
| Microcrystalline cellulose | 5.0% w/w |
| Povidone K30 | 6.0% w/w |
| Colloidal silicon dioxide | 0.3% w/w |
| Magnesium stearate | 0.5% w/w |

The components, with the exception of the colloidal silicon dioxide and the magnesium stearate, are blended together in a suitable mixer. The powder is then mixed with demineralised water until a granule is formed. The granule is dried and screened to obtain a satisfactory particle size. The screened granule is then blended with the colloidal silicon dioxide and the magnesium stearate.

Bilayer tablets containing 5 mg of methadone hydrochloride weighing 300 mg and containing 100 mg of Part A and 200 mg of Part B, and 9 mm in diameter are produced on a tablet press by a two stage compression procedure.

EXAMPLE 13

| Part A | |
|---|---|
| Pethidine hydrochloride | 25.0% w/w |
| Lactose | 39.0% w/w |
| Maize starch | 27.5% w/w |
| Povidone K30 | 5.0% w/w |
| Sodium starch glycollate | 3.0% w/w |
| Magnesium stearate | 0.5% w/w |

The pethidine hydrochloride, lactose, povidone and some of the maize starch are mixed together in a blender and then mixed with a paste prepared from the remaining starch and demineralised water until a granule is formed. The granule is dried and passed through a screen to obtain a satisfactory particle size. The screened granule is then blended with the sodium starch glycollate and the magnesium stearate.

| Part B | |
|---|---|
| Hydroxypropylmethylcellullose (100,000 cp) | 40.0% w/w |
| Calcium hydrogen phosphate | 19.2% w/w |
| Lactose | 29.0% w/w |
| Microcrystalline cellulose | 5.0% w/w |
| Povidone K30 | 6.0% w/w |
| Colloidal silicon dioxide | 0.3% w/w |
| Magnesium stearate | 0.5% w/w |

The components, with the exception of the colloidal silicon dioxide and the magnesium stearate, are blended together in a suitable mixer. The powder is then mixed with demineralised water until a granule is formed. The granule is dried and screened to obtain a satisfactory particle size. The screened granule is then blended with the colloidal silicon dioxide and the magnesium stearate.

Bilayer tablets containing 50 mg of pethidine hydrochloride weighing 400 mg and containing 200 mg of Part A and 200 mg of Part B, and 10 mm in diameter are produced on a tablet press by a two stage compression procedure.

EXAMPLE 14

| Part A | |
|---|---|
| Phenytoin sodium | 69.7% w/w |
| Potato starch | 16.5% w/w |
| Sodium lauryl sulphate | 1.0% w/w |
| Acacia | 2.5% w/w |
| French chalk powdered | 9.3% w/w |
| Magnesium stearate | 1.0% w/w |

All of the components, except the sodium lauryl sulphate and the magnesium stearate, are mixed together in a blender and then granulated with an 80% v/v solution of ethanol in demineralised water until a satisfactory granule is formed. The granule is dried and passed through a screen to obtain a satisfactory particle size. The screened granule is then blended with the sodium lauryl sulphate and magnesium stearate.

| Part B | |
|---|---|
| Phenobarbitone sodium | 45.0% w/w |
| Potato starch | 32.0% w/w |
| Sodium lauryl sulphate | 1.0% w/w |
| Acacia | 3.0% w/w |
| French chalk powdered | 18.0% w/w |
| Magnesium stearate | 1.0% w/w |

All of the components, except the sodium lauryl sulphate and the magnesium stearate, are mixed together in a blender and then granulated with an 80% v/v solution of ethanol in demineralised water until a satisfactory granule is formed. The granule is dried and passed through a screen to obtain a satisfactory particle size. The screened granule is then blended with the sodium lauryl sulphate and magnesium stearate.

| Part C | |
|---|---|
| Hydroxypropylmethylcellullose (100,000 cp) | 40.0% w/w |
| Calcium hydrogen phosphate | 19.2% w/w |
| Lactose | 29.0% w/w |
| Microcrystalline cellulose | 5.0% w/w |
| Povidone K30 | 6.0% w/w |
| Colloidal silicon dioxide | 0.3% w/w |
| Magnesium stearate | 0.5% w/w |

The components, with the exception of the colloidal silicon dioxide and the magnesium stearate, are blended together in a suitable mixer. The powder is then mixed with demineralised water until a granule is formed. The granule is dried and screened to obtain a satisfactory particle size. The dried granule is then blended with the colloidal silicon dioxide and the magnesium stearate.

Trilayer tablets containing 100 mg of phenytoin sodium and 50 mg of phenobarbitone sodium, weighing 455 mg and containing 144 mg of Part A, 111 mg of Part B and 200 mg of Part C, and 11 mm in diameter are produced on a tablet press by a three stage compression procedure.

Comparative Tests

Test 1

Conventional tablets containing 7.5 mg zopiclone and weighing 165 mg, according to the formula in Table 1, were prepared using a simple wet granulation technique. Bilayer zopiclone tablets containing hydroxypropylmethylcellulose as a gelling agent (100,000 cp) were prepared according to Example 1. The tablet under examination was coarsely crushed using a pestle and mortar and extracted with 2 ml of hot or cold water, or an aqueous solution of acetic acid, citric acid or of isopropanol, for 10 minutes. Attempts were made to filter the solutions through a 0.2 micron filter using a syringe. If successful, the concentration of zopiclone in the filtrate was then determined using spectrophotometric measurement at 307 nm. The results are summarised in Table 2.

TABLE 1

Conventional tablet formulation containing 7.5 mg zopiclone

| Material | Quantity per 100 grams product (g) |
|---|---|
| Zopiclone | 4.55 |
| Lactose | 19.45 |
| Calcium hydrogen phosphate | 36.36 |
| Maize starch | 36.36 |
| Sodium starch glycollate | 3.03 |
| Magnesium stearate | 0.24 |

TABLE 2

Extraction over a 10 minute period of control zopiclone tablets and bilayer zopiclone tablets containing 100,000 cp hydroxypropylmethylcellulose using 2 ml of extraction medium.

| Extraction Media | Dosage Form | Concentration in Filtrate (mg/unit dose) | Percentage zopiclone extracted from tablet |
|---|---|---|---|
| Distilled water | Conventional Tablet | 0.40 | 5.5 |
|  | Bilayer Tablet | x | 0 |
| Citric acid solution 5% w/v | Conventional Tablet | 4.45 | 56.2 |
|  | Bilayer Tablet | x | 0 |
| Acetic acid solution 4% w/v | Conventional Tablet | 5.92 | 68.6 |
|  | Bilayer Tablet | x | 0 |
| isopropanol solution 70% v/v | Conventional Tablet | 3.76 | 32.9 |
|  | Bilayer Tablet | x | 0 | x = not filterable

The results clearly show that, whilst quite substantial levels of zopiclone can be extracted from a conventional tablet, especially when acidic media are used, no filterable solution is present when the bilayer zopiclone tablets of the invention containing a gelling agent are treated with the same medium. The potential for abuse of the tablet product is therefore strictly limited.

Test 2

Dissolution studies were performed on conventional and bilayer zopiclone tablets, as used in Test 1, using the standard USP paddle method operating at a temperature of 37° C. and a rotation speed of 50 r.p.m., with 0.01M hydrochloric acid as the dissolution medium.

Tablets were also prepared according to the formula in Table 3 using standard mixing, granulation and compression techniques to provide a single layer tablet weighing 168 mg and containing 7.5 mg of zopiclone and the hydroxypropylmethylcellulose gelling agent (10,000 cp).

A comparison of the dissolution results is shown in Table 4.

TABLE 3

Single Layer Tablet Formulation Containing 7.5 mg Zopiclone and a Hydroxypropylmethylcellulose Gelling Agent.

| Material | Quantity per 100 grams product (g) |
|---|---|
| Zopiclone | 4.46 |
| Lactose | 14.88 |
| Calcium hydrogen phosphate | 38.69 |
| Maize starch | 17.86 |
| Hydroxypropylmethylcellulose (10,000 cp) | 14.90 |
| Sodium starch glycollate | 8.90 |
| Magnesium stearate | 0.30 |

TABLE 4

Dissolution data for conventional zopiclone tablets without a gelling agent, bilayer zopiclone tablets containing a hydroxypropylmethylcellulose (100,000 cp) gelling agent and tablets where zopiclone and hydroxypropylmethylcellulose (10,000 cp) are combined in a single layer.

| Dosage Form | Approximate Times to Release Stated Percentage of Zopiclone | | |
|---|---|---|---|
| | 50% | 70% | 90% |
| Conventional Zopiclone Tablet | 3 mins | 5 mins | 23 mins |
| Bilayer Tablet with Gelling Agent | 3 mins | 4 mins | 32 mins |
| Single Layer Tablet with Gelling Agent | 2 hours | No further release up to 12 | |

The results show that the rate of release of zopiclone from the conventional and bilayer tablets is very similar and that no significant delay is imparted by the presence of the gelling agent. From these results it can be anticipated that the in vivo release and absorption of the two forms would be similar.

The test also demonstrates that the presence of the gelling agent and zopiclone in a single layer results in a serious deterioration of drug release with only 50% of the drug being released after two hours with the remaining drug being trapped in the tablet matrix.

Comparison of the results for the bilayer and the single layer tablets where the zopiclone and gelling agent are mixed together shows that despite the inclusion of a higher viscosity grade of hydroxypropylmethylcellulose (100,000 cp compared to 10,000 cp) release from the bilayer tablet is unaffected.

In summary, it has been demonstrated that the invention provides an abuse resistant tablet which has the dissolution properties of conventional tablets whereas inclusion of the gelling agent in a single layer with the drug substance causes a serious retardation of release.

What is claimed is:

1. An abuse resistant tablet containing two or more layers comprising (1) a drug and (2) a gelling agent, wherein the gelling agent has a viscosity within the range of about 4,000 cp to about 100,000 cp, wherein the tablet consists essentially of either (i) separate layers one stacked on top of the other in a sandwich arrangement or (ii) a core layer comprising gelling agent enclosed by one or more layers comprising one or more drugs, wherein essentially all the drugs are contained in a separate layer or layers from all gelling agents.

2. A tablet according to claim 1 in which the gelling agent has a viscosity within the range of about 10,000 cp to about 100,000 cp.

3. A tablet according to claim 1 in which the gelling agent is present in a gelling layer, and in which the proportion of gelling agent by weight in the gelling layer is from about 20 to about 60%.

4. A tablet according to claim 3 in which the proportion of gelling agent by weight in the gelling layer is from about 30 to about 50%.

5. A tablet according to claim 3 in which the total amount of gelling layer in the tablet is about 50 to about 80% by weight.

6. A tablet according to claim 1 in which the gelling agent is selected from the group consisting of a modified cellulose, sodium alginate, alginic acid, tragacanth, polyacrylic acid and xanthan, guar, locust bean and karaya gums.

7. A tablet according to claim 6 in which the gelling agent is selected from the group consisting of hydroxypropylmethylcellulose, carboxymethylcellulose, methylcellulose and xanthane gum.

8. A tablet according to claim 7 in which the gelling agent is hydroxypropylmethylcellulose.

9. A tablet according to claim 1 in which the drug is selected from the group consisting of analgesics, hypnotics and anxiolytics.

10. A tablet according to claim 9 in which the drug is selected from the group consisting of zopiclone, temazepam, diazepam, zolpidem, codeine, methadone, pethidine, phenytoin and phenobarbitone.

11. A tablet according to claim 10 in which the drug is zopiclone.

12. A tablet according to claim 1 having two layers in which one layer comprises a drug and the other layer comprises a gelling agent.

13. A bilayer tablet in which one layer comprises the drug zopiclone and the other layer comprises a gelling agent.

14. A bilayer tablet according to claim 13 in which the gelling agent is hydroxypropylmethylcellulose.

15. A tablet according to claim 1 also comprising a coating.

16. A tablet according to claim 1 having an active layer comprising the drug and a gelling layer comprising the gelling agent, in which the active and gelling layers are substantially identical in color and appearance.

17. A method of treating a patient requiring an analgesic, hypnotic or anxiolytic drug, which method comprises administering to said patient said drug comprised within a tablet according to claim 1.

18. A process for the preparation of a tablet comprising an active layer comprising a drug and a gelling layer comprising a gelling agent, in which the process comprises the following steps:

(i) compressing a first layer from a suitable powder; and (ii) compressing one or more additional layers on top of the first layer or subsequent layers to form a bilayer or multilayer tablet.

19. A process for the preparation of a tablet comprising an active layer comprising a drug and a gelling layer comprising a gelling agent, in which the process comprises the following steps:

(i) preparing the gelling layer by compressing a suitable powder; and (ii) enclosing the gelling layer with one or more active layers by means of a tablet press.

20. A tablet comprising a gelling layer, which gelling layer comprises a gelling agent, and an active layer, which active layer comprises a drug, wherein the gelling agent does not impart any significant delay in the rate of drug release and wherein essentially no drug is extractable from the tablet when the tablet is contacted over ten minutes with water.

21. A process for the preparation of a tablet according to claim 18 further comprising applying a coating to the combined layers.

22. A tablet formed according to the process of claim 18.

* * * * *